United States Patent [19]
Bazin et al.

[11] Patent Number: 5,090,402
[45] Date of Patent: Feb. 25, 1992

[54] MASSAGING APPLIANCE

[75] Inventors: Roland Bazin, Vitry Sur Seine; Etienne Soudant, Antony; Gérard Obadia, Montrouge; Jean-Pierre Laugier, Antony; Louis Marcotte, Chevilly Larue, all of France

[73] Assignee: L'Oreal, Paris, France

[21] Appl. No.: 559,378

[22] Filed: Jul. 25, 1990

Related U.S. Application Data

[63] Continuation-in-part of Ser. No. 231,028, Aug. 11, 1988, abandoned.

[30] Foreign Application Priority Data

Aug. 12, 1987 [FR] France .................. 87 11461

[51] Int. Cl.$^5$ ............................................ A61H 15/00
[52] U.S. Cl. .................................... 128/57; 128/24.4; 128/65
[58] Field of Search ................... 128/21.1–24.5, 128/57, 65

[56] References Cited

U.S. PATENT DOCUMENTS

| | | | |
|---|---|---|---|
| 564,258 | 7/1896 | Rossbach | 128/24.5 |
| 693,063 | 2/1902 | Preston | 128/24.5 |
| 784,024 | 3/1905 | Barrett | 128/57 |
| 1,532,463 | 4/1925 | Winterfield | 128/24.4 |
| 1,539,299 | 5/1925 | Cheney | 128/57 |
| 1,811,764 | 6/1931 | Sherwood | 128/24.4 |
| 1,948,067 | 2/1934 | Carreno et al. | 128/24.5 |
| 2,285,105 | 6/1942 | Bacher | 128/24.3 |
| 2,480,029 | 8/1949 | Jozsy | 128/24.4 |
| 3,081,769 | 3/1963 | Ackerman | 128/67 |
| 4,010,742 | 3/1977 | Kim | 128/24.4 |
| 4,126,128 | 11/1978 | Takahashi | 128/24.3 |
| 4,166,457 | 9/1979 | Jacobsen et al. | 128/639 |
| 4,175,551 | 11/1979 | D'Haenens et al. | 128/24.4 |
| 4,811,726 | 3/1989 | Goncalves et al. | 128/57 |

FOREIGN PATENT DOCUMENTS

| | | | |
|---|---|---|---|
| 0001833 | 5/1978 | European Pat. Off. | |
| 770825 | 9/1934 | France | |
| 1286023 | 9/1962 | France | |
| 2449612 | 9/1980 | France | |
| 2483225 | 4/1981 | France | |
| 370525 | 7/1963 | Switzerland | 128/65 |
| 387960 | 2/1933 | United Kingdom | 128/24.4 |
| 938138 | 10/1963 | United Kingdom | |

Primary Examiner—V. Millin
Assistant Examiner—Joe H. Cheng
Attorney, Agent, or Firm—Cushman, Darby & Cushman

[57] ABSTRACT

An appliance for manual use for massaging a cutaneous covering, comprising, on the one hand, a reservoir (1) containing the product to be applied, and integral with a gripping element (2), the reservoir comprising a movable wall (4), so as to adapt its internal volume (9) to the quantity of product contained and, on the other hand, an applicator element (3) constituted by a sole (6) cooperating with the reservoir (1) and comprising at least one ball (7) held in a housing (8), which communicates with the internal volume of the reservoir (1) through at least one opening. The appliance also comprises a direct current source (12), which is situated in the said gripping element (2) and whose poles are each connected to one electrode, the first electrode (13) being a conductive covering which covers the wall of the gripping element (2) and the second electrode (14) being constituted by a conductive film which is in permanent contact with the product situated in the reservoir (1).

6 Claims, 3 Drawing Sheets

MASSAGING APPLIANCE

This is a continuation-in-part of application Ser. No. 07/231,028, filed on Aug. 11, 1988, now abandoned.

The present invention concerns a massaging appliance for manual use which comprises balls serving to massage the cutaneous covering and simultaneously allows the massaging product to penetrate into this cutaneous covering by way of iontophoresis.

It is known that in order to apply cosmetic products such as deodorants for example, applicators can be advantageously used comprising a reservoir and whose dispensing element is constituted by at least one ball which is caused to roll over the skin: this ball is, on the one hand, in contact with the product contained in the reservoir and on the other, with the cutaneous covering. Thus, because of the rolling of the ball, the ball zone previously coated with the treatment product comes to be applied against the cutaneous covering: this product is, by this very reason, spread over the surface of the cutaneous covering and can eventually penetrate into it. The applicators of this type have a twofold advantage: to allow an easy distribution of a product in the form of a cream or having a pasty consistency and to avoid any risk of injury or lesion of the skin when the applicator is manipulated, because of the rounded shape of the ball. Such applicators are described in particular in the documents FR-A-2 449612 and FR-A-2 483 225.

To cause the penetration of a cosmetic or pharmaceutical composition, an iontophoretic appliance can also be used which comprises tow electrodes, each connected to one of the poles of a direct current electric source, the active substance in the form of an ionizable solution being trapped in an absorbent material in contact with one of the electrodes. Under the action of the direct current, the ions coming from the ionizable solution are displaced; some of these ions, anions or cations according to the polarity of the electric source to which the absorbent material is connected, can thus penetrate into the skin under the effect of the direct current action. The electrode associated with the absorbent material is fixed mechanically or by way of adherence to the skin.

An appliance of this type has already been described in the European Patent EP-A-0001833; this document describes a manual massaging appliance comprising an electric pulse source making it possible to cause a massaging surface to vibrate. To enhance the effect of such a massage without prejudice to operating safety, this appliance is provided with a heating plate covering the massaging surface connected to an electric source and can be put into operation by manipulating an electric switch. Moreover, an electrode carrier plate is attached to the massaging surface. It will be observed that such a massaging appliance does not include any reservoir for the product to be applied, which makes it necessary to deposit the treatment product by means of another device. Moreover, the vibrating massage is not very powerful.

In the British patent GB-A-938138, there has also been described an iontophoretic appliance comprising a ball serving to apply an electrolyte and which also has a massaging effect; the ball constitutes one electrode of the appliance and for this purpose, it is constituted of a metallic material. It follows therefrom that if the ball is immobile or dry, that is to say, without the product, a considerable eletric current can pass between the ball and the user's skin with the risk of burning which is all the higher, the smaller the contact surface. Moreover, the ball electrode being in contact with the air, is subjected to oxidation phenomena which produces a modification of the operating characteristics of the appliance with time, and this all the more so, since the electric contact between a fixed part and a movable part is always difficult to obtain.

Finally, the use of metal balls in an appliance intended for the treatment of the skin is not to be recommended, because the application of these balls to the skin produces a sensation of cold which is disagreeable for the user.

The main object of the present invention is to propose a massaging appliance for manual use which makes it possible to combine the advantages of massaging appliances with balls and of iontophoretic devices, so as to apply a cosmetic or pharmaceutical substance to a cutaneous covering and to cause it to penetrate into it, whilst avoiding the above mentioned drawbacks.

Another object of the invention is to propose a massaging appliance for manual use having an increased efficiency, which is easy to manufacture and inexpensive.

The object of the present invention is therefore an appliance for manual use for massaging a cutaneous covering comprising on the one hand, a reservoir containing the product to be applied and integral with a gripping element and on the other hand, an applicator element constituted by a sole cooperating with this reservoir and comprising at least one ball held in a housing which communicates with the internal space of the reservoir via at least one opening, the said appliance comprising a direct current source which is situated in the said gripping element and whose poles are connected respectively to a first and a second electrode, the first electrode being a conductive covering which covers the wall of the gripping element, characterised in that the second electrode is constituted by a conductive film which is in permanent contact with the product to be applied situated in the reservoir, the said reservoir comprising a movable wall so as to adapt its internal volume to the quantity of the product contained.

It should be noted that the device according to the invention such as defined above makes it possible to avoid all the above mentioned drawbacks presented by similar state of the art devices; in particular, contrary to what is happening in the device of the above mentioned British patent GB-A-938138. the passing of the current can, in the appliance according to the invention, only be effected via the product to be applied, which obviates all risk of burning the user's skin; when there is not longer any product, no current can pass.

Preferably, according to one mode of embodiment, the movable wall is constituted by the sole which can slide along the lateral walls of the reservoir. In a first variant, the second electrode is situated against the wall of this reservoir and is advantageously of an annular shape. In a second variant, the ball (or balls) is (or are) held in its (or their) housing(s) by the second electrode which is constituted by a perforated electrically conductive sheet fixed to the sole.

According to another mode of embodiment, the movable wall is constituted by an elastically deformable element bearing against the bottom of the reservoir and capable of filling the major portion of this reservoir, the second electrode covering this electrically deformable element and the applicator element surmounting the reservoir.

Preferably, this appliance comprises a cap cooperating with the gripping element and surmounting the applicator element and the reservoir.

Advantageously, the internal volume of the reservoir communicates with the outside via a filler device.

Provision can also be made for the direct current source to be associated with a current regulator capable of limiting the ionization current.

As for the wall of the gripping element, it is preferably made of a conductive material so as to constitute the first electrode.

The description that follows and which is not of a restrictive nature, should be read with reference to the attached figures wherein:

FIG. 3 is a cross sectional view of a massaging appliance according to a third mode of embodiment;

Figure 1:
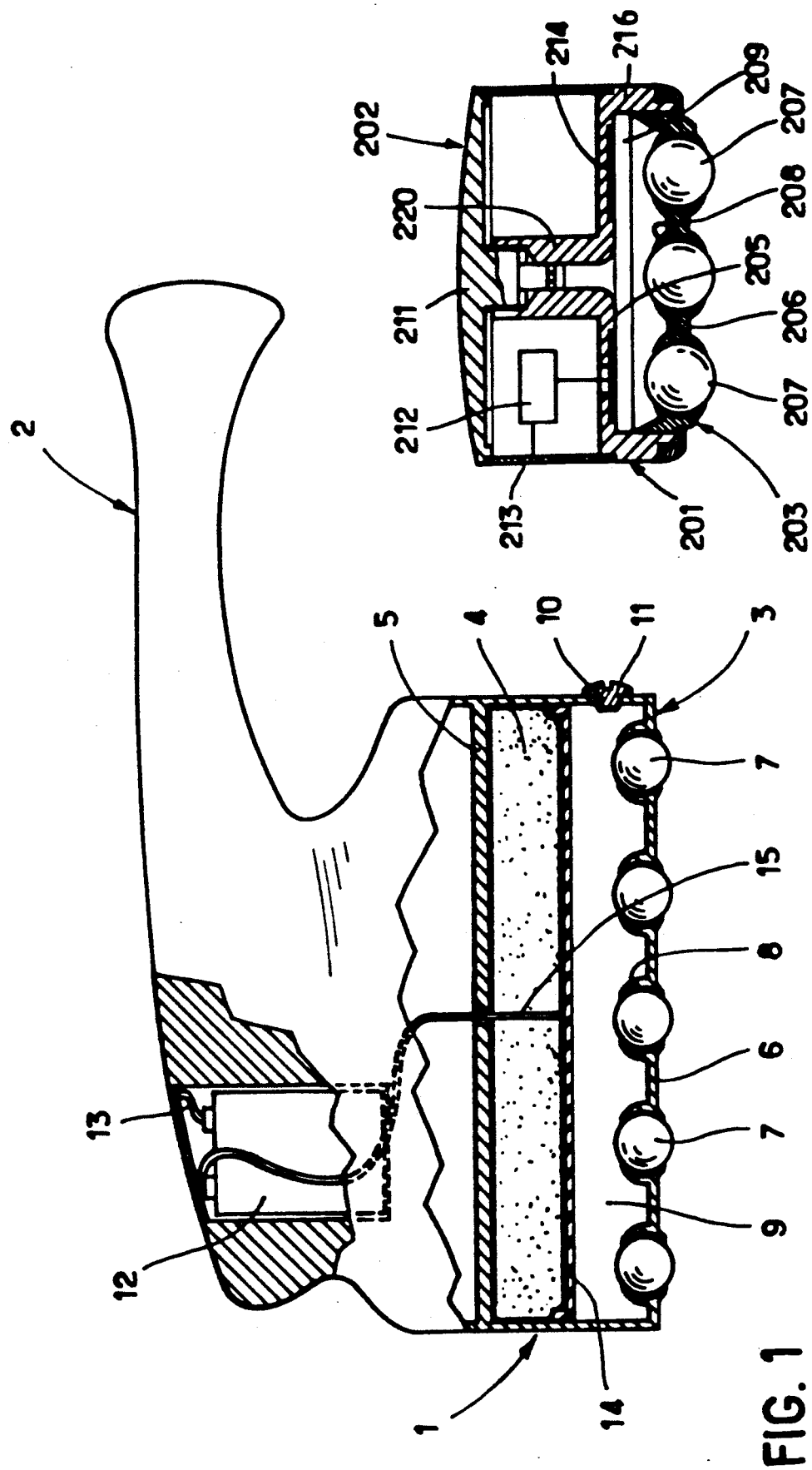
FIG. 1 is a partly stripped side view of a massaging appliance according to a first mode of embodiment of the present invention.

As may be seen in FIG. 1, a massaging appliance according to the present invention, comprises a reservoir 1 integral with a handle-shaped gripping element 2, and an applicator element 3 surmounting this reservoir 1.

This substantially cylindrically shaped reservoir 1 contains an elastically deformable element 4 which is formed by a foam resting on the bottom 5 of the reservoir 1 and capable of filling the whole internal volume 9 of the reservoir 1. The bottom 5 of the reservoir 1 is situated on the opposite side to the applicator element 3.

The applicator element 3 is constituted by a sole 6 comprising balls 7 which are each held in a housing 8. Each housing 8 communicates in the known way through at least one opening with the internal volume 9 of the reservoir 1. This internal volume 9 which is comprised between the foam 4 and the sole 6, contains the ionizable product to be applied which is introduced through an opening 10 provided with a stopper 11, situated on the lateral wall of the reservoir 1.

This massaging appliance also comprises a direct current source 12, which is constituted by a battery and which is situated in the gripping element 2 substantially in the portion of this element surmounting the reservoir 1. This battery 12 is connected via one of its terminals to a first electrode 13 constituted by a conductive covering which covers the gripping element 2 and via its other terminal to a second electrode 14 which covers the surface of the foam 4 in contact with the product to be applied present in the internal space 9. This second electrode 14 is connected to the battery 12 by means of a conductor wire 15, which passes through the top 5 substantially at is centre.

For using this massaging appliance, the ionizable product to be applied is introduced into the internal space 9 through the opening 10; then this opening is obturated by means of the stopper 11. When the user applies the balls of this appliance to the skin, the polarity connected to the gripping element is also connected to this user's skin, and the electric circuit is closed by the product film covering the balls 7. Since the product to be applied is in contact with the second electrode 14 it is ionized and is applied in an ionized form to a cutaneous covering by the balls 7. The elastically deformable element 4 allows the second electrode 14 to be kept always in contact with the product to be applied present in the internal volume 9.

Figure 2:
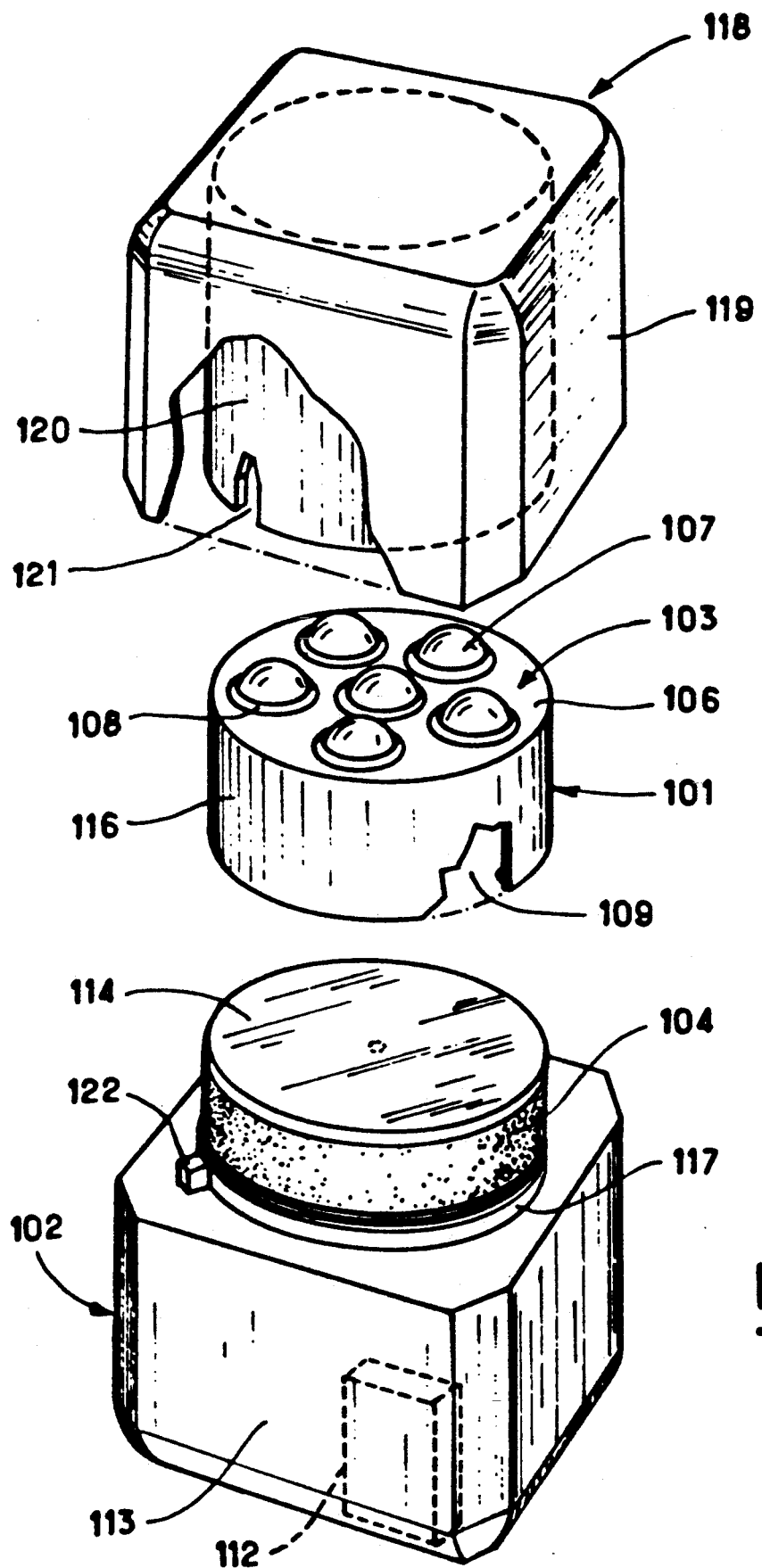
FIG. 2 is an exploded view of a massaging appliance according to a second mode of embodiment.

FIG. 2 represents a second mode of embodiment of a massaging appliance according to the present invention. The elements similar to those of the first mode of embodiment have the same reference numeral increased by 100.

This massaging appliance comprises a reservoir 101 integral with a gripping element 102 and an applicator element 103 surmounting this reservoir 101. In point of fact, the reservoir 102, is delimited by a cylindrical skirt 116 and by the applicator element 103.

The gripping element 102 comprises a base 117 whereon the lower portion of the skirt 116 delimiting the reservoir 101 comes to be catch engaged. On this base 117, an elastically deformable element 104 is disposed, which rests on this base 117 and which constitutes the bottom of the reservoir 101. The element 104 is capable of completely filling the internal volume 109 of the reservoir 101.

The applicator element 103 is constituted by a sole 106 comprising balls 107 each held in a housing 108, each housing 108 communicates in the known way via at least one opening with the internal space 109 of the reservoir 101. This internal volume 109 which is comprised between the foam 104 and the applicator surface 108, contains the ionizable product to be applied which can be introduced before the reservoir 101 is catch engaged on the base 117.

In the gripping element 102 which is substantially parallelepiped shaped, a battery 112 is disposed, whereof one terminal is connected to a first electrode 113 constituted by a conductive cover covering the external surface of this gripping element 102 and whose other terminal is connected to a second electrode 114 which covers the surface of the foam 104 present in the internal volume 109.

The massaging appliance according to this - mode of embodiment also comprises a cap 118 which rests on the gripping element 102 and protects the balls 107 of the applicator element 103. This cap comprises an external skirt 119 whose shape is identical with that of the gripping element 102 in order to form a pleasing unit, and an internal cylindrical skirt 120, the two skirts being connected by the top of the cap. This internal cylindrical skirt 120 comprises a slot 121 parallel to the axis of the cap 118; this slot comes to surmount a stop 122 provided at the edge of the base 117 in this example of the embodiment. The functioning of this second mode of embodiment is identical with that of the first mode of embodiment described above.

FIG. 3 represents a third mode of embodiment of a massaging appliance according to the present invention. The elements similar to those of the first mode of embodiment, have the same reference numeral increased by 200.

This massaging appliance comprises a reservoir 201 integral with a gripping element 202 and an applicator element 203 which cooperates with this reservoir. In point of fact, the reservoir 201 is, in this example of the embodiment, delimited by a cylindrical skirt 216, a bottom 205 situated on the side of the gripping element 202 and the applicator element 203.

The applicator element 203 is constituted by a sole 206 comprising balls 207 each held in a housing 208.

Each housing 208 communicates in the known way through at least one opening with the internal space 209 of the reservoir 201. This internal volume 209 which is comprised between the bottom 205 and the sole 206 contains the ionizable product to be applied.

The applicator element 203 slides along the internal face of the cylindrical skirt 216 in such a way that the sole 206 is always in contact with the product contained in the reservoir 201. In other words, thanks to this sliding action of the movable wall or sole 206 the internal volume 209 of the reservoir 201 is being continuously adapted to the quantity of product contained.

A battery 212 is disposed in the gripping element 202 which is substantially cylindrical, whereof one terminal is connected to a first electrode 213 constituted by a conductive cover covering the external cylindrical surface of this gripping element 202 and whose other terminal is connected to a second electrode 214 which is disposed on the surface of the bottom 205 in contact with the product to be applied, present in the internal volume 209. This electrode is in this example, annular in shape.

The gripping element 202 comprises on the opposite side to the bottom 205, a stopper 211 and a hollow median column 220, whereof one end issues in the internal space 209 of the reservoir 201, the other cooperating with the stopper 211.

To use this massaging appliance, the ionizable product to be applied is introduced into the reservoir 201 through the hollow column 220 after the stopper 211 has been removed. Once filled, the stopper 211 is put back. When a user applies the balls 207 of this appliance to the skin, the polarity connected to the gripping element is also connected to the skin of this user and the electric circuit is closed by the product film covering the balls 207. Since the product to be applied is in contact with the second electrode 214, it is ionized and is applied in ionized form to the cutaneous covering by the balls 207. As some of the product is being applied, the applicator element 203 slides along the internal surface of the cylindrical skirt 216 towards the bottom 205 in such a way that the volume of the internal space 209 is being continuously adapted to the quantity of the product present in this space; the second electrode 214 is thus always in contact with some of the product to be applied.

Figure 4:
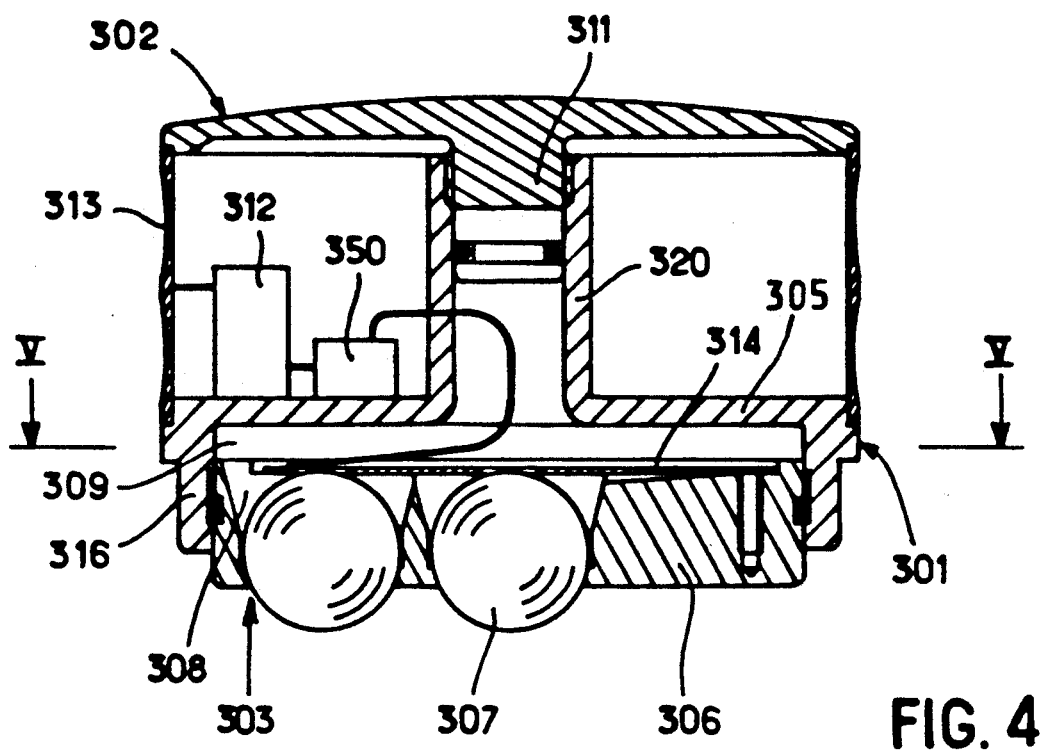
FIG. 4 is an axial cross section of a massaging appliance according to a fourth mode of embodiment.
Figure 5:
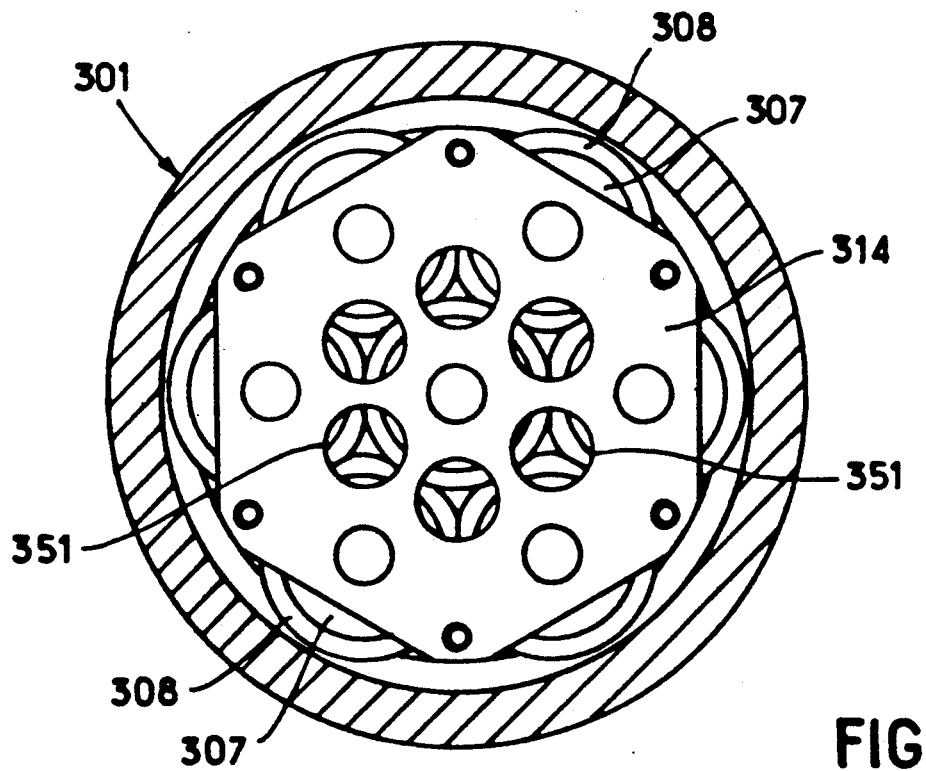
FIG. 5 is a cross section along V-V of FIG. 4.

FIGS. 4 and 5 represents a fourth mode of embodiment of the appliance according to the invention. The elements similar to those of the first mode of embodiment are designated by the same reference numerals increased by 300. This appliance comprises a reservoir 301 integral with a gripping element 302 and an applicator element 303 which cooperates with this reservoir. The reservoir 301 is delimited by a cylindrical skirt 316, a bottom 305 situated on the side of the gripping element 302 and the applicator element 303.

The applicator element 303 is constituted by a sole 306 comprising balls 307 each held in a conical housing 308 by means of a perforated metal sheet 314. The sheet 314 comprises a circular perforation opposite each ball 307 and perforations 351 between the various balls. The portion of the reservoir 301 situated on the side of the sheet 314 where the gripping element 302 is located, contains the ionizable product to be distributed, the said product coming into contact with the balls 307, in particular by passing through the perforations 351. The applicator element 303 slides along the internal surface of the skirt 316, so that in the course of use, the sole 306 compresses the product to be distributed irrespective of the quantity remaining.

A battery 312 has been placed in the substantially cylindrical gripping element 302 one terminal whereof is connected to a first electrode 313 constituted by the metallic lateral wall of the gripping element 302 and whose other terminal is connected to a second electrode constituted by the metallic sheet 314 via a current regulator 350.

The gripping element 302 comprises along its axis a median hollow column 320 which, on the one side, issues in the central zone of the bottom 305 and on the other side, is obturated by a threaded stopper 311 forming the cap of the gripping element.

The mode of use of this embodiment is exactly the same as in the case of the embodiment of FIG. 3. Depending on the force exerted during the massage, the quantity of the applied product is adjusted, thanks to the conical shape of the housing 308 and to the elastic deformation of the perforated metallic sheet 314. The presence of the regulator 350 ensures perfect safety of the appliance in use.

Each of the embodiments of the present invention contemplates that the balls 7, 207, 307 are made of a non-conductive material of a plastic or of wood.

We claim:

1. A manual appliance for massaging a cutaneous covering comprising: a reservoir containing a product to be applied and being integral with a gripping element; and an applicator element including a sole cooperating with said reservoir and comprising a plurality of balls each held in a recess provided in said sole and which communicates with the internal volume of said reservoir through said recess, each said ball being non-conductive, a direct current source which is situated in said gripping element and having poles which are connected respectively to a first and a second electrodes, wherein the first electrode is a conductive covering which covers the wall of the gripping element, wherein the second electrode is a movable conductive sheet located in said reservoir so as to be in contact with said product situated in the reservoir, and wherein said reservoir comprises a bottom, an elastically deformable wall which is movable so as to adapt its internal volume to the quantity of the product contained and lateral side walls which are fixed and rigid, wherein said movable wall is against said bottom of said reservoir and occupies a portion of said reservoir and wherein said second electrode covers said movable wall and said applicator surmounts said reservoir.

2. An appliance according to claim 1 further comprises a cap cooperating with the gripping element and surmounting the applicator element and the reservoir.

3. An appliance according to claim 1, wherein internal volume of the reservoir communicates with the outside through a filler element.

4. An appliance according to claim 1, wherein the direct current source is associated with a current regulator.

5. An appliance according to claim 1, wherein said ball is made of a plastic material.

6. An appliance according to claim 1, wherein said ball is made of wood.

* * * * *